(12) United States Patent
Collins et al.

(10) Patent No.: US 6,342,358 B1
(45) Date of Patent: Jan. 29, 2002

(54) HUMAN TELOMERASE RNA ELEMENTS

(75) Inventors: Kathleen Collins; James R. Mitchell, both of Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/645,713

(22) Filed: Aug. 24, 2000

(51) Int. Cl.[7] .............................. C12Q 1/68; C12N 5/00; G01N 33/53; C07H 21/02; C07K 1/00

(52) U.S. Cl. ........................... 435/6; 435/325; 435/375; 435/7.8; 536/23.1; 536/23.5; 536/24.1; 530/350

(58) Field of Search .............................. 536/24.1, 24.2, 536/23.1, 24.3, 23.5; 435/6, 375, 325, 7.8; 530/350; 436/86

(56) References Cited

U.S. PATENT DOCUMENTS 5,776,679 A * 7/1998 Villeponteau et al. ......... 435/6

6,015,710 A * 1/2000 Shay et al. ................. 435/375

* cited by examiner

*Primary Examiner*—W. Gary Jones
*Assistant Examiner*—Cynthia B. Wilder
(74) *Attorney, Agent, or Firm*—Richard Aron Osman

(57) ABSTRACT

The invention provides methods and compositions relating to discrete elements of human telomerase and human telomerase RNA. In one embodiment, the invention provides a polynucleotide comprising only one element of human telomerase RNA, wherein the element consists of SEQ ID NO:1, residues 241–330. Such human telomerase RNA elements may be employed in mixtures with a human telomerase polypeptide such as TERT or dyskerin, wherein the polypeptide and polynucleotide specifically interact, and such mixtures may be employed in methods for identifying modulators of a human telomerase polypeptide—human telomerase RNA interaction.

14 Claims, 2 Drawing Sheets

HUMAN TELOMERASE RNA ELEMENTS

This work was supported by the National Institutes of Health, Grant No. GM 54198. The government may have rights in any patent issuing on this application.

INTRODUCTION

1. Field of the Invention

The field of the invention is functional elements of human telomerase—an enzyme important in cell growth.

2. Background of the Invention

Telomeres are the dynamic nucleoprotein complexes that cap the ends of linear chromosomes. They prevent undesirable chromosome rearrangements and protect against genomic instability and the associated risk of carcinogenesis (Artandi and DePinho, 2000). Telomeres can also function as a mitotic clock that counts cell divisions by the gradual erosion of telomeric sequence. Telomere shortening forces cultured human primary cells to stop dividing when a critical minimum telomere length is reached (Colgin and Reddel, 1999). This entry into senescence acts as a protective checkpoint, guarding against genomic instability induced by telomere loss.

Many cellular factors are required to maintain telomere stability, including the telomere binding proteins that orchestrate a higher order telomeric chromatin structure (Collins, 2000). At a regulatory level, however, changes in telomere length appear to be accomplished primarily by activation or inhibition of telomerase. The telomerase ribonucleoprotein (RNP) extends chromosome 3' ends by addition of one strand of tandem DNA repeats (Greider, 1995). Telomerases in all species share at least two components essential for catalytic activity: the telomerase reverse transcriptase protein (TERT) and the telomerase RNA (Bryan and Cech, 1999). Although TERTs share the reverse transcriptase (RT) active site motifs of viral RTs (Lingner et al., 1997), they are unique in their stable association with a telomerase RNA that contains the template for telomeric repeat synthesis Greider and Blackburn, 1989). Telomerase RNAs range in size from about 150–200 ucleotides (nt) in ciliates to greater than 1000 nt in yeasts.

In humans, misregulation of telomerase activity can have dire consequences. Telomerase activation accompanies tumorigenesis and is important for the continued viability of cultured human tumor cells (Kim et al., 1994; Artandi and DePinho, 2000; Collins, 2000). However, recent studies have suggested that telomerase activation in at least some human cell types is also essential for normal growth and development. Premature mortality caused by the X-linked disease dyskeratosis congenita (DKC) results from proliferative deficiencies and an increased risk of cancer in tissues which are normally highly regenerative, such as the skin and blood (Dokal, 1999). Cells from DKC patients have reduced levels of telomerase RNP and hastened telomere shortening (Mitchell et al., 1999b). This suggests that telomerase activation in highly proliferative tissues may be necessary to suppress potential genomic instability and to guarantee enough renewal capacity for a typical human lifespan. Together, these findings reveal that telomerase activation and inhibition must be carefully balanced to meet the proliferative demands of normal cells while at the same time guarding against the potential for unbridled proliferation of tumors. As a result, pharmacological methods for activating or restraining telomerase activity in vivo would both be useful.

The human telomerase RNA (hTR) is transcribed by RNA polymerase II and processed at its 3' end to yield a mature transcript of 451 nt (Feng et al., 1995; Zaug et al., 1996; Mitchell et al., 1999a). The template for reverse transcription lies near the 5' end of the molecule and specifies incorporation of the sequence TTAGGG to chromosome ends. In a previous study, we identified hTR primary sequence elements that are required for the stability and 3' end processing of recombinant hTR in vivo (Mitchell et al., 1999a). Surprisingly, these elements form part of a structural motif shared with H/ACA small nucleolar (sno)RNAs, an RNA family that functions in the maturation of ribosomal RNA by directing cleavage and pseudouridine ($\Psi$) formation (Tollervey and Kiss, 1997). Hybridization of a snoRNA to target RNA specifies the site of modification, while protein components of the stable snoRNP catalyze the reaction itself. Phylogenetic comparison of 35 vertebrate telomerase RNAs confirmed that the H/ACA motif is a universally conserved feature that is not present in ciliate or yeast telomerase RNAs (Chen et al., 2000). The 3' half of hTR as bounded by the elements of the H/ACA motif (nt 211–451) can accumulate independently of the full-length molecule in vivo (Mitchell et al., 1999a). We refer to this region as the hTR H/ACA domain (see FIG. 1). When the hTR H/ACA domain is replaced with a heterologous H/ACA snoRNA, the chimeric RNA accumulates but does not support telomerase activity (Mitchell et al., 1999a). Therefore, sequences within the hTR H/ACA domain are critical for telomerase activity independent of the requirement for hTR stability in vivo.

Here, we define distinct motifs within the human telomerase RNA that contribute to telomerase RNP accumulation and activity. We find that hTR precursor processing, mature RNA accumulation, and H/ACA protein association are inseparably linked and require the consensus H/ACA motif elements within the H/ACA domain. Furthermore, we demonstrate that two regions within the telomerase RNA are required for telomerase activity in vivo and in vitro. One of these regions contains the template for reverse transcription as expected (hTR nt 1–209); the other is a telomerase-specific element within the H/ACA domain (hTR nt 241–330). Surprisingly, we find that both of these regions interact independently with TERT and bind to TERT in a largely noncooperative manner. Thus, a vertebrate-specific telomerase RNA motif physically separable from the template is required for telomerase activity. This work reveals an unexpected functional requirement for two distinct telomerase RNA-TERT interactions within the same telomerase RNP and establishes a fundamental difference between the structure of ciliate and vertebrate telomerase RNPs.

Relevant Literature

See U.S. Pat. Nos. 5,917,025 and 5,770,422.

SUMMARY OF THE INVENTION

Telomerase inhibition has utility as a clinical treatment for a broad range of human cancers (treated by telomerase inhibition) and age- or disease-induced cellular proliferative deficiencies (treated by telomerase activation). Requirements for telomerase function at a structural level have hitherto remained largely unknown. Here, we demonstrate the structural requirements for function of the essential human telomerase RNA component (hTR) in vivo and in vitro. Two types of function for RNA elements are discriminated. First, we have identified RNA elements that are essential for RNA stability in vivo but are dispensable for catalytic activity in vitro. Second, we have identified RNA motifs that are critical for catalytic activity in vivo and in vitro.

The first category, RNA elements essential for RNA stability in vivo, includes all elements of the consensus H/ACA motif in proper sequence context (5' terminal stem: nts 211–214 paired to 367–370; H box: unpaired nts 372–377; 3' terminal stem: nts 381–384 paired to 440–443; ACA box: unpaired nts 446–448) and one additional element (3' stem-loop: nts 411–418). Cellular accumulation of stable hTR, dependent on the H/ACA motif elements described above, is coincident with the association of RNA with H/ACA proteins (as assayed by association with the protein dyskerin, as a cooperative assembly of the proteins dyskerin, hNhp2, hNop10 and additional cooperative or noncooperative assembly of the protein hGAR1.

The second category, RNA elements essential for catalytic activity both in vivo and in vitro includes a region containing the template (nts 1–208 in vivo and in vitro; in vitro element minimized to nts 44–186) and a second region termed IH1 (nts 241–330 in vivo and in vitro; in vitro element minimized to 253–322 without 271–285). Each of these RNA elements binds to the telomerase reverse transcriptase protein (TERT) independently, both in vivo and in vitro. However, binding of both elements is required for catalytic activity, in vivo and in vitro.

The first 656 amino acids of hTERT are sufficient for binding to both RNA elements required for catalytic activity with efficiency similar to full-length hTERT in vivo. In vivo methods for stable recombinant RNA production and recombinant protein-RNA interaction assays, modifiable to provide in vivo reporter assays for RNA structure and/or RNA-protein interaction and described below and in Cheng et al. (1999) Mol Cell Biol 19, 567–576.

In vitro methods for analysis of requirements for recombinant RNA activity and recombinant RNA-protein interaction, optimization of telomerase catalytic activity by RNA minimization, trans complementation, and titration; and production of reconstituted telomerase RNPs limited in activity by a specific RNA binding requirement are described below.

This work enables screening technology to develop compounds with clinical utility for telomerase inhibition or activation. First, important RNA structures have been determined. Thus, screens for molecules that interact with an essential hTR sequence and/or structure are used to identify candidate modulators of telomerase stability and/or activity. Second, protein interactions mediated by essential hTR elements have been determined. Thus, screens for molecules that affect protein-RNA interaction are also used to identify candidate modulators of telomerase stability and/or activity.

Improvements/distinctions from current screening technology using nucleotide incorporation activity assays:

1. Catalytic activity in vivo on telomeres and in vitro on oligonucleotide substrates have been demonstrated to have different requirements for substrates and enzyme components; therefore, molecules that inhibit activity in vitro may not do so similarly in vivo. In addition, the active site of an endogenous telomerase holoenzyme RNP may differ from that of partially purified holoenzyme or recombinant core enzyme isolated or produced in vitro. In contrast, with the disclosed functional domains, RNA or protein-RNA interaction based screens can use RNA elements demonstrated to be required in vivo and furthermore known to be required in a particular structural context.

2. Because at least some features of the telomerase active site are shared by polymerases in general, a large number of activity inhibitors will have multiple targets in vivo. In contrast, the disclosed telomerase RNA motifs are either entirely unique (the ones required for activity) or at least partially distinct in sequence (the ones required for stability) from all other known human RNAs.

3. Molecules attained by screening for activity inhibition and by screening for RNA structure or protein-RNA interaction impact both have potential to reduce the level of telomerase enzyme or enzyme activity. However, binding of an activity inhibitor is more likely to be reversible, whereas disruption of a RNA structure or protein-RNA interaction may also lead to mislocalization or turnover and thus more permanent inactivation.

4. The new technology can be used to improve catalytic activity-based screens, by allowing smaller RNAs to be used at defined concentrations in sensitized activity assays with recombinant telomerase protein(s).

Accordingly, the invention provides methods and compositions relating to discrete elements of human telomerase and human telomerase RNA. In one embodiment, the invention provides a polynucleotide comprising only one element of human telomerase RNA, wherein the element consists of SEQ ID NO:1, residues 241–330. Such human telomerase RNA elements may be employed in mixtures with a human telomerase polypeptide such as TERT or dyskerin, wherein the polypeptide and polynucleotide specifically interact, and such mixtures may be employed in methods for identifying modulators of a human telomerase polypeptide - human telomerase RNA interaction. In a particular embodiment, such methods comprise the steps of incubating the mixture with a candidate agent under conditions whereby, but for the presence of said agent, said polypeptide specifically binds said polynucleotide at a reference affinity; and detecting the binding affinity of the polypeptide to the polynucleotide to determine an agent-biased affinity, wherein a difference between the agent-biased affinity and the reference affinity indicates that the agent modulates the binding of the polypeptide to the polynucleotide. The binding affinity may be detected directly by solid phase binding assay or inferentially as telomerase catalytic activity, and the mixture may be in vitro or within a viable cell.

DETAILED DESCRIPTION OF SPECIFIC EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or.

hTR H/ACA domain sequence requirements for accumulation and activity in vivo. To investigate the sequence requirements for hTR accumulation and activity in vivo, we utilized our previously characterized recombinant hTR expression system (Mitchell et al., 1999a). Recombinant hTR was marked with a sequence tag to permit specific detection by Northern blot hybridization and expressed by transient transfection of telomerase-positive, adenovirus-transformed human embryonic kidney (293) cells. Like endogenous hTR, recombinant hTR was expressed from an RNA polymerase II mRNA-type promoter. Both endogenous and recombinant forms of mature hTR migrate as doublets through denaturing 5% polyacrylamide gels, likely due to sequence-specific folding (Mitchell et al., 1999a). A slower-migrating, recombinant hTR species was also observed. Based on its length, it appears to be a 3' unprocessed precursor polyadenylated at a vector-derived polyadenylation signal downstream of the hTR gene (described in the text as "precursor"). In some experiments, recombinant hTR also contained an altered template directing the synthesis of TTGGGG repeats rather than the endogenous TTAGGG to allow the discrimination of endogenous from recombinant telomerase RNA activity.

Figure 1:
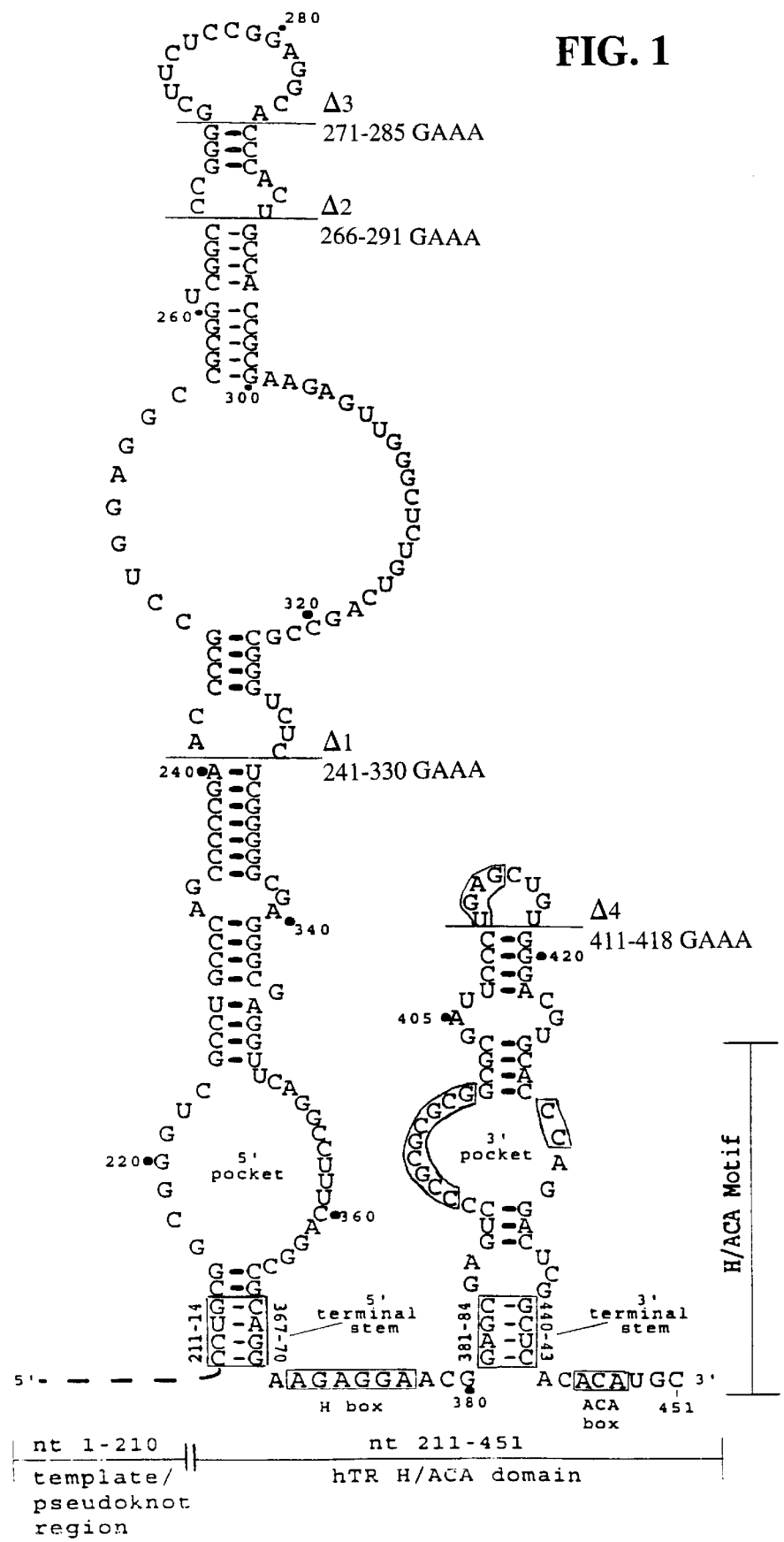
FIG. 1. Secondary structure of the hTR H/ACA domain. (nt 211–451). Residues mutagenized in this study are highlighted. Δ1–Δ4 indicate deletions, with the sequence above the line replaced by the stable tetraloop sequence GAAA. Conserved elements of the H/ACA motif include the 5' and 3' potential pseudouridylation pockets, 5' and 3' terminal stems, and H and ACA boxes. The position of the 20 nt inserted sequence tag is indicated by a filled carat between nt 354 and nt 355. Filled ovals indicate conserved base pairs supported by phylogenetic comparison (Chen et al., 2000); hollow ovals indicate putative base pairs.

The 3' end of hTR contains the consensus "hairpin-hinge-hairpin-tail" structural elements of the H/ACA motif (FIG. 1). Conserved primary sequence elements known as the H box (ANANNA) and the ACA box (ACA) are located within the hinge and tail regions, respectively. Both are required for accumulation of H/ACA snoRNAs in yeast and human cells (Balakin et al., 1996; Ganot et al., 1997b). Previously, we showed that consensus H and ACA box elements are also critical for hTR accumulation in vivo: substitutions of conserved nucleotides within the H box (AGAGGA to UGUGGU) or the ACA box (ACA to UGU or UCA) inhibit recombinant hTR accumulation, although substitution of variable H box nucleotides (AGAGGA to AUAUUA) has no effect (Mitchell et al., 1999a). Here, we tested the requirements for additional elements of the H/ACA motif. Single (AGAGGA to UGAGGA) or double (to UGUGGA) nucleotide substitutions in the H box allowed precursor synthesis but prevented accumulation of either the mature recombinant RNA or recombinant telomerase activity. Thus, as observed for the H/ACA snoRNAs tested previously, substitution of even a single conserved residue within the H or ACA box element is sufficient to inhibit hTR accumulation in vivo.

The conserved duplex structures immediately 5' of both H and ACA boxes (FIG. 1) can also be critical for accumulation of yeast and human H/ACA snoRNAs (Balakin et al., 1996; Bortolin et al., 1999). To examine whether base-pairing of the analogous hTR "terminal stems" is important for hTR accumulation, we made individual and combinatorial substitutions at the base of the 5' and 3' hairpin stems (FIG. 1). Substitution of 4 nt on either side of the 3' terminal stem (nt 381–384 GAGC to CUCG; nt 440–443 GCUC to CGAG) prevented detectable accumulation of recombinant hTR or telomerase activity. Compensatory mutations that restored base-pairing potential partially rescued hTR accumulation and activity. These results suggest that hTR accumulation requires the conserved 3' terminal stem structure as previously observed for H/ACA snoRNAs.

Accumulation of intron-derived H/ACA snoRNAs requires an intact 5' terminal stem, but accumulation of H/ACA snoRNAs that are transcribed from their own gene and capped at their 5' end does not (Bortolin et al., 1999). In either case, an intact 5' terminal stem is still required for the assembled RNP to be active in the catalysis of Ψ formation. Similar to capped H/ACA snoRNAs, substitution of 4 nt on the left side of the hTR 5' terminal stem (FIG. 1, nt 211–214 CCUG to GGAC) did not prevent accumulation of the full-length molecule but did reduce telomerase activity dramatically. It also prevented independent accumulation of the hTR H/ACA domain, which is processed from full-length hTR and thus has lost its 5' cap structure. The recombinant full-length 5' L hTR migrated as a single band instead of a doublet, suggesting that a sequence within the 5' hairpin contributes to an alternate folding during electrophoresis. Substitution of the right side of the 5' terminal stem (FIG. 1, nt 367–370 CAGG to GUCC) had minimal impact on full-length hTR accumulation or activity. This likely is due to an alternate base pairing that restored a 5' stem pairing between nt 367–370 and nt 219–222. This postulated alternate pairing is consistent with the accumulation of a 5'R H/ACA domain smaller than the wild-type. Compensatory mutations restoring the potential for 5' terminal stem pairing at its original position yielded a full-length hTR that was active and a combination of the two H/ACA domains. Together, these data suggest that the H/ACA motif sequence requirements for hTR accumulation and activity are indistinguishable from those of an H/ACA snoRNA transcribed from its own gene. Formation of both terminal stems appears to be necessary for the production of a functional telomerase RNP in vivo.

A final conserved feature of H/ACA snoRNAs is the presence of two pseudouridylation pockets, one in each hairpin. Each pocket consists of a bulge bracketed by helical stems, with the base of the top stem at a conserved 13–16 nt distance 5' of the corresponding H or ACA box (Ganot et al., 1997a). Base pairing of a snoRNA with a target RNA across the top of one or both pockets establishes the site-specificity of Ω formation (Ganot et al., 1997a). Although the lower stem, which corresponds to the H/ACA motif 5' or 3' terminal stem, is required for H/ACA RNA stability (see above), the upper stem is required only for catalysis of Ψ formation (Bortolin et al., 1999). Potential pseudouridylation pockets are present in both hairpins of the hTR H/ACA domain (FIG. 1). Experiments with the human H/ACA snoRNA U65 suggest that Ψ formation directed by the two pockets is highly cooperative, such that both pockets must be intact in order for either of them to catalyze the isomerization reaction (Bortolin et al., 1999). However, it is not known whether hTR guides Ψ formation in vivo. To determine whether pocket structure or sequence is important for hTR accumulation or telomerase activity, we tested two mutations in the hTR 3' pocket. Substitution of nt 391–399 (FIG. 1) on the left side of the pocket with the 5 nt sequence UGGGU was intended to allow several alternate base-pairing configurations that would shrink or eliminate the pocket. This substitution inhibited the production of recombinant full-length hTR, the hTR H/ACA domain, and telomerase activity to below detectable levels. In contrast, substitution of two potential target hybridization nucleotides on the right side of the 3' pocket (nt 430–431 CC to AA) had no detectable effect on RNA accumulation or telomerase activity. The right side of the recombinant hTR 5' pocket contains the 20 nt sequence tag between hTR nt 354 and 355. This insertion, like the 3' pocket substitutions, would disrupt any target hybridization function but has no detectable effect on hTR accumulation or telomerase activity (Mitchell et al., 1999a). Thus, although some structural features of at least the 3' pocket appear to be important, the sequence of either pocket can be altered without detectably affecting hTR accumulation or telomerase activity.

The hTR H/ACA domain is larger in size than most H/ACA snoRNAs, due to the presence of an extended 5' hairpin structure (FIG. 1). We designed three truncations of this region that removed different amounts of telomerase-specific sequence while leaving the conserved elements of the H/ACA motif intact (Δ1–Δ3). Each truncation removed sequence above a predicted stem structure and replaced it with a stable tetraloop (GAAA). The largest deletion (Δ1, nt 241–330) had no detectable effect on the accumulation of full-length hTR or the hTR H/ACA domain but abolished telomerase activity. Similarly, a smaller deletion of the distal 26 nt of the 5' stem (Δ2, nt 266–291) abolished detectable telomerase activity without affecting hTR accumulation. In contrast, a 15 nt deletion (Δ3, nt 271–285) had no detectable effect on telomerase RNA accumulation or activity. These results define a region in the 5' hairpin structure of the hTR H/ACA domain (nt 241–270 and nt 286–330) that is required for telomerase activity in vivo, distinct from the consensus elements of the H/ACA motif that are required for RNA accumulation.

Sequence requirements for hTR association with dyskerin and TERT. For the telomerase RNA variants that accumulated in vivo but were catalytically inactive, we asked whether inactivity could be correlated with the failure to associate with a particular telomerase protein. We tested the sequence requirements for hTR association with two proteins previously shown to be components of the telomerase RNP, dyskerin and TERT. Dyskerin is common to both the telomerase RNP and H/ACA snoRNPs, whereas TERT is a telomerase-specific protein (Mitchell et al., 1999b). By cotransfection of 293 cells, we simultaneously expressed HA epitope-tagged dyskerin (HA-dyskerin) and FLAG epitope-tagged TERT (FLAG-TERT) with one hTR variant at a time. Extracts of transfected cells were immunopurified on HA or FLAG antibody resin, from which RNA was prepared and analyzed by Northern blot hybridization with an oligonucleotide complementary to the recombinant hTR sequence tag. Because 293 cells contain abundant endogenous dyskerin and some endogenous TERT, only a percentage of the recombinant hTR population became associated with the tagged recombinant proteins. As a control, hTR was not recovered on antibody resins in the absence of the tagged proteins.

As demonstrated previously (Mitchell et al., 1999b), recombinant full-length hTR associated with HA-dyskerin. The independently stable hTR H/ACA domain also associated with HA-dyskerin, presumably through an interaction with the H/ACA motif. All of the hTR variants that accumulated as mature RNA were equally capable of association with HA-dyskerin. This was true for the full-length RNAs as well as their independently stable H/ACA domains. Thus, all telomerase RNA-containing RNPs incorporated dyskerin regardless of the state of their catalytic activity. The observed correlation of mature hTR stability with dyskerin association parallels the previously observed requirement for the Saccharomyces cerevisiae dyskerin homolog Cbf5 p in H/ACA snoRNA stability (Lafontaine et al., 1998).

FLAG-TERT also associated with full-length recombinant hTR as demonstrated previously (Mitchell et al., 1999b). Much to our surprise, the independently stable hTR H/ACA domain also associated with FLAG-TERT. As described above for HA-dyskerin, each full-length hTR variant also copurified with FLAG-TERT. However, in contrast with the HA-dyskerin immunopurification results, the efficiency of full-length RNA immunopurification by FLAG antibody resin varied, as did the state of association of the independently stable hTR H/ACA domain. A strong correlation was observed between hTR variants that were catalytically inactive and those that displayed a reduced association with TERT. The amount of full-length, inactive Δ1, Δ2 and 5'L hTR variants that was associated with TERT was less than that observed for full-length wild-type hTR. In addition, for the Δ1, Δ2 and 5'L hTR variants, an independently stable hTR H/ACA domain was either not observed (5'L) or failed to associate with TERT (Δ1 and Δ2). Thus, deletion of the hTR H/ACA domain 5' stem region that is required for activity decreased the ability of the full-length RNA to bind TERT and eliminated the ability of the H/ACA domain alone to bind TERT. In contrast, the amount of full-length, catalytically active Δ3, 5'R and 5'R/L hTR variants associated with TERT was indistinguishable from that observed for wild-type hTR, and their independently stable H/ACA domains were also equally capable of TERT association. These results demonstrate that the sequences within hTR nt 241–330 that are required for telomerase activity are also required for optimal TERT association in vivo.

We considered the possibility that the independently stable hTR H/ACA domain was actually being tethered to TERT indirectly by a full-length telomerase RNA and thus was not bound to TERT in a truly independent fashion. Either endogenous or recombinant full-length hTR could potentially bridge such an interaction between TERT and the hTR H/ACA domain through a putative multimerization of H/ACA domains. To test whether the hTR H/ACA domain does interact independently with TERT, we assayed the association of recombinant hTR variants with TERT in extracts of transiently-transfected VA 13 cells, which lack endogenous hTR (Bryan et al., 1995). Epitope-tagged TERT was coexpressed with either full-length hTR, the hTR H/ACA domain alone or hTR Δ1, which lacks the region required for optimal TERT association. Similar percentages of full-length hTR and the hTR H/ACA domain copurified with FLAG-TERT. hTR Δ1 remained predominantly in the immunopurification supernatant, although a small amount was observed in the immunopurified bound fraction in a longer exposure. The apparent decrease in association of the fact that VA13 cells produce substantially less recombinant RNA than the same number of 293 cells transfected in parallel due to reduced transfection efficiency. In any case, these results clearly demonstrate that TERT can associate with the hTR H/ACA domain independently of the hTR 5' end (nt 1–209), and that optimal TERT-hTR interaction depends on an element within nt 241–330. Because this region of the hTR H/ACA domain is dispensable for hTR stability and thus separable from H/ACA motif function, we refer to it as the hTR H/ACA inserted hairpin 1 element (IH1) following the convention for IH elements that are 5' of the H box in H/ACA snoRNAs (Ganot et al., 1997b). This region includes the telomerase-specific conserved regions (CRs) 4 and 5 (hTR nt 243–265 and 292–326) and additional sequences critical for telomerase activity (those removed in hTR Δ2 but not hTR Δ3 above).

IH1 element activates a heterologous H/ACA RNA domain in vivo. We have shown that deletion of the hTR IH1 element (nt 241–330) in full-length hTR (above) or substitution of the entire hTR H/ACA domain with the heterologous human H/ACA snoRNA U64 (Mitchell et al., 1999a) results in the accumulation of a stable RNA that is catalytically inactive. To determine if IH1 is the only element of the hTR H/ACA domain required specifically for telomerase activity in vivo, we inserted this element into the hTR-U64 chimera. An Nhe I restriction site was created in the U64 5' terminal hairpin loop (U64 nt 29–34), into which hTR IH1 flanked by Nhe I linkers was inserted (creating hTR-U64-IH1). As a control, IH1 was inserted in the opposite orientation as well (creating hTR-U64-αIH1). Wild-type hTR and chimeric hTR-U64, hTR-U64-IH1, and hTR-U64-αIH1 expression constructs with the altered template were cotransfected with FLAG-TERT in 293 and VA13 cells. FLAG-tagged telomerase RNPs were immunopurified from extracts of transfected cells and assayed for wild-type (WT) and altered-template (AT) telomerase activity catalyzed by the endogenous and recombinant telomerase RNAs, respectively. A similar amount of endogenous telomerase activity was immunopurified from each 293 transfection extract; VA13 cells have no endogenous active telomerase. Assays specific for recombinant telomerase activity from the altered template confirmed that the hTR-U64 chimera is catalytically inactive as demonstrated previously (Mitchell et al., 1999a). Insertion of the sense but not antisense hTR IH1 element rescued recombinant telomerase activity in 293 cells to a level close to that obtained with recombinant full-length hTR. Activation of the recombinant hTR-U64 chimera by insertion of the IH1 element was also evident in VA13 cells and thus did not require the presence of endogenous hTR. We conclude that IH1 contains a region that is required for telomerase activity in vivo. Furthermore, our data demonstrate that the conserved elements of the hTR H/ACA motif, including the H and ACA box primary sequence elements, 5' and 3' terminal stems, and Ψ guide pockets, can all be substituted simultaneously with a heterologous H/ACA motif.

Each chimeric RNA was monitored for FLAG-TERT association. In 293 cell extracts, full-length hTR and hTR-U64-IH1 associated equally well with immunopurified TERT, whereas hTR-U64 and hTR-U64-αIH1 associated with TERT at a reduced efficiency. In VA13 cells, hTR-U64-IH1 also interacted with TERT to a greater extent than hTR-U64. The apparent decrease in association of hTR-U64 with TERT when comparing VA13 cell assays to 293 cell assays may derive from the reduced transfection efficiency of VA 13 cells relative to 293 cells. Together, these results indicate that although hTR nt 1–209 and the IH1 element of the H/ACA domain can associate independently with TERT, the combination of these two interactions is required for optimal TERT interaction. Both interactions are required for telomerase activity in vivo.

Sequence requirements for IH1-TERT interaction and telomerase activation in vivo.

Within the IH1 element, studies described above revealed that deletion of nt 271–285 (Δ3) had no effect on telomerase activity whereas a slightly larger deletion of nt 266–291 (Δ2) eliminated activity entirely. To further deduce the sequence requirements for telomerase activity within IH1, we created additional variants in the context of full-length, altered-template hTR for in vivo analysis. None of the changes described below affected the accumulation of hTR, as expected from the accumulation of hTR Δ1 in which this region is deleted entirely.

Figure 2:
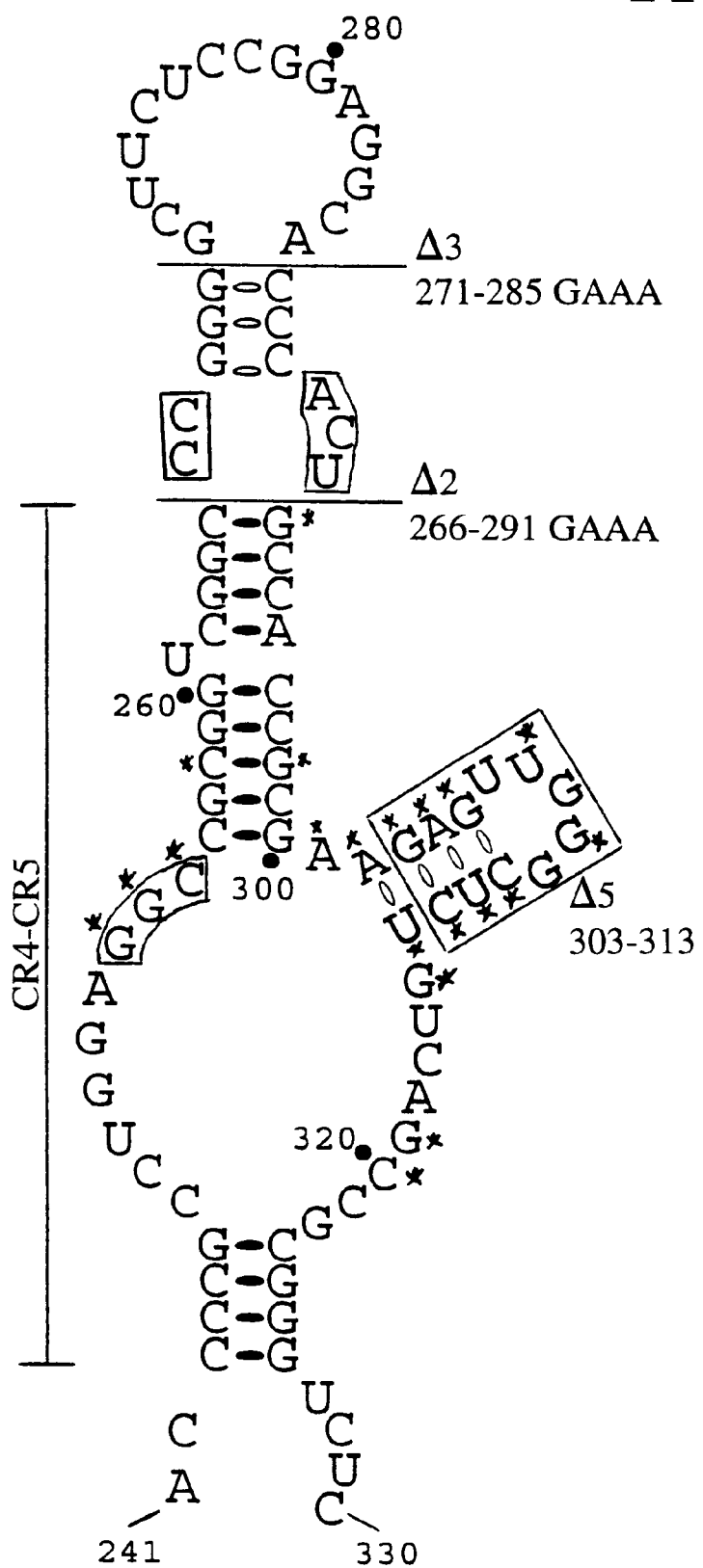
FIG. 2. Mutational analysis of the IH1 element. (A) Potential secondary structure of the hTR IH1 element. Filled ovals indicate phylogenetically conserved base pairs; hollow ovals indicate putative base pairs. Asterisks designate residues conserved in all known vertebrate telomerase RNAs, and the previously defined CR4–CR5 region is indicated (Chen et al., 2000). Substituted and deleted residues are indicated and highlighted.

A structure for IH1 is shown in FIG. 2. Duplex formation between nt 302–305 and nt 311–314 cannot be confirmed by phylogenetic comparison due to the lack of covariation (Chen et al., 2000), but each of the 35 vertebrate telomerase RNAs has the potential to form this short stem. Deletion of nt 303–313 (Δ5) abolished recombinant telomerase activity as well as the interaction of the hTR H/ACA domain with TERT. Substitution of the conserved 253–255 GGC with UUA reduced telomerase activity and the association of the hTR H/ACA domain with TERT. Like 253–255 UUA, 289–291 UAA reduced the association of the hTR H/ACA domain with TERT although telomerase activity associated with this variant was intermediate between that of 253–255 UUA and wild-type. The substitution 266–267 CC to AA had no effect on telomerase activity or TERT association. These results indicate that numerous sequence elements both inside and outside of the conserved CR4-CR5 region are required for optimal TERT association and telomerase activity in vivo.

RNA sequence requirements for catalytic activity in vitro. Telomerase activity can be reconstituted in rabbit reticulocyte lysate (RRL) using only hTR and TERT (Weinrich et al., 1997; Beattie et al., 1998), bypassing certain in vivo hTR requirements such as precursor RNA processing. We used the RRL expression system to ask if the hTR sequence requirements for catalytic activity of a minimal recombinant RNP in vitro are the same as those that we defined above for the endogenous RNP in vivo. We initially tested full-length telomerase RNAs previously characterized in vivo; those capable of reconstituting telomerase activity were predicted to generate a single TRAP assay product due to the presence of the altered template. The hTR variants Δ1 and Δ2 and the hTR-U64 chimera were all inactive in vitro paralleling our in vivo results. Insertion of the hTR IH1 element into the hTR-U64 chimera rescued a wild-type or greater level of telomerase activity, when assayed at the same RNA concentration as wild-type hTR. Insertion of the antisense IH1 element failed to activate telomerase in vitro as in vivo. Mutations in the conserved 3' terminal stem of the H/ACA motif had no effect in vitro. Likewise, mutation of a telomerase-specific sequence motif in the 3' H/ACA hairpin (hTR Δ4) that is also required for RNA stability in vivo (see below) had no effect in vitro. We conclude that although the H/ACA motif and the top of the 3' H/ACA hairpin included within CR7 (Chen et al., 2000) are necessary for hTR accumulation in vivo, they are dispensable for telomerase activity in vitro. In contrast, IH1 is required for optimal telomerase activity both in vivo and in vitro.

The minimal region of hTR necessary for reconstitution of telomerase activity in RRL was defined in previous studies as either hTR nt 1–160 (Beattie et al., 1998) or nt 33–325 Tesmer et al., 1999). It was also reported that hTR fragments 33–147 and 164–325 activate elomerase in trans (Tesmer et al., 1999), although the efficiency of "transactivation" relative to activation by full-length hTR was not investigated. Because these transactivating RNA fragments can potentially base pair in two conserved regions, reforming the pseudoknot and part of the conserved P1 duplex (Chen et al., 2000), it is possible that the observed transactivation of telomerase requires such a bridging interaction. Guided by our in vivo results, we investigated the RNA sequence requirements for in vitro telomerase activity as well as the potential for RNA function in trans. For the latter, we used RNA fragments that are not predicted to engage in base-pairing interactions (hTR nt 1–209, 207–451). TERT was expressed in RRL, assembled with various hTR fragments and assayed for telomerase activity. No telomerase activity was detected in the absence of hTR or in the presence of hTR nt 207–451 alone. A very low level of telomerase activity was observed with high concentrations of hTR nt 1–209 alone. Telomerase transactivation by hTR nt 1–209 and nt 207–451 was nearly as effective as activation by full-length hTR. A titration of nt 1–209 in the presence of 1 μM nt 207–451 or a titration of nt 207–451 in the presence of 1 μM nt 1–209 appeared to saturate for telomerase activation at slightly higher RNA concentrations than required for saturation with the full-length RNA. The maximal amount of telomerase activation achieved with full-length relative to transactivating hTR fragments, however, was similar in this and other experiments.

To determine whether the IH1 element of the H/ACA domain is sufficient for the observed transactivation by nt 207–451 in vitro, we tested this element (including hTR nt 241–330) in combination with 1 $\mu$M nt 1–209 for stimulation of telomerase activity. Titration of IH1 accomplished an equivalent or better transactivation than the same molar concentration of nt 207–451, and with a similar concentration dependence. We conclude that the hTR IH1 element contains all of the residues within the hTR H/ACA domain required specifically for telomerase activity in vitro as well as in vivo. Because hTR nt 1–209, nt 207–451, and IH1 displayed a similar concentration-dependence for telomerase transactivation, it appears that each of these hTR fragments has a similar affinity for TERT in vitro.

The above experiments were performed in the presence of RRL, because molecular chaperones present in the lysate have been shown to enhance recombinant telomerase activity (Holt et al., 1999). However, because other factors in RRL could potentially bind exogenously added telomerase RNAs, reducing their effective concentrations and altering their apparent affinities for TERT, we repeated the experiment with TERT immunopurified from RRL before the addition of telomerase RNA. The results were nearly identical, except that less telomerase activity was produced in the absence of RRL at any given RNA concentration.

Finally, we tested the order-of-addition requirements for assembly and activation of the telomerase RNP with TERT, hTR nt 1–209 and IH1. HA-TERT was expressed in RRL, purified on HA antibody resin, and assembled in the presence of RRL with full-length hTR, hTR nt 1–209, IH1, or nt 1–209 and IH1. Following this initial assembly reaction, TERT-RNA complexes were washed to remove unbound RNA. Telomerase activity was readily detected with full-length hTR or the combination of nt 1–209 and IH1 but not with nt 1–209 or IH1 alone. Thus, assembled telomerase RNPs subjected to repeated washing remained stable in the absence of RRL and the amount of telomerase activated with 1 $\mu$M of full-length RNA was similar to that obtained with 1 $\mu$M each of nt 1–209 and IH1.

TERT-RNA complexes assembled independently with hTR nt 1–209 or IH1 were washed and then assembled a second time with fresh RRL and the appropriate transactivating RNA. After washing a second time, a similar amount of telomerase activity was observed in samples subjected to different orders of hTR fragment addition. However, if TERT-RNA complexes assembled separately with hTR nt 1–209 and IH1 were washed and then the antibody resins were mixed in the presence of fresh RRL, no transactivation was observed. This demonstrated that both RNA fragments must interact with the same TERT molecule to stimulate telomerase activity. It also controlled for the adequate removal of unbound RNAs in our washing procedure. The experiment was repeated using affinity-purified TERT in the absence of RRL during any RNP assembly step with identical results, except that a lower overall level of telomerase activity in each sample. We conclude that hTR nt 1–209 and the IH1 element of the H/ACA domain can bind TERT independently and in a largely noncooperative manner in vitro as well as in vivo. Furthermore, these RNA fragments stimulate nearly as much telomerase activity in trans as they do in cis, in the context of the full-length telomerase RNA.

Accumulation of hTR in vivo requires an H/ACA motif. The 3' half of hTR shares the hairpin-hinge-hairpin-tail secondary structure common to H/ACA snoRNAs (Ganot et al., 1997b). All of the conserved elements of the H/ACA motif are contained within the independently stable hTR H/ACA domain, including H and ACA box primary sequence elements, 5' and 3' terminal stems, and potential pseudouridylation pockets (FIG. 1). Each of these elements was required for the accumulation of an independently stable H/ACA domain in vivo, although the 5' terminal stem could be displaced to an alternate pairing. In full-length hTR, the 5' terminal stem was dispensable for accumulation but was required for telomerase activity. All of the above H/ACA motif structural requirements for in vivo telomerase RNA accumulation and activity closely parallel the in vivo requirements for H/ACA snoRNA accumulation and activity (Bortolin et al., 1999).

Identification of an inserted hairpin element in the H/ACA motif required for telomerase activity. Previous studies revealed that the heterologous H/ACA snoRNA U64 can substitute for the hTR H/ACA domain to allow the accumulation of an RNA chimera in vivo (Mitchell et al., 1999a). However, the RNP formed with the chimeric RNA does not have detectable telomerase activity as assayed by TRAP. This suggests that either the U64 moiety adversely affects the folding of hTR nt 1–209, or that telomerase-specific elements in the hTR H/ACA domain are required for activity. Indicating the latter, we identified an element in the hTR H/ACA domain (IH1) that restores telomerase activity to the hTR-U64 chimera. Furthermore, we demonstrated that the hTR IH1 element mediates an independent, stable interaction between the hTR H/ACA domain and TERT, and that this interaction is required for optimal association of full-length hTR with TERT in vivo. In vitro, the combination of IH1 and hTR nt 1–209 in trans is sufficient for maximal catalytic activity.

Although IH elements of various sizes are common to H/ACA snoRNAs (Ganot et al., 1997b), this is the first time that an IH element has been demonstrated to provide a distinct function. The evolutionarily conserved CR4-CR5 region (Chen et al., 2000) is contained within the IH1 element and plays a role in mediating IH1 interaction with TERT. In vivo, deletions and substitutions of nucleotides within and immediately outside of these conserved regions affected TERT interaction and telomerase activity.

Because the U64 H/ACA snoRNA was interchangeable with all but IH1 of the hTR H/ACA domain in the hTR-U64-IH1 chimera, any role for the conserved CR7 sequence motif at the top of the 3' stem (Chen et al., 2000) remains unclear. Interestingly, close examination of the U64 sequence revealed that the absolutely conserved hTR CR7 residues 410 C, 418 U, and 420 G are represented in somewhat similar context in U64, along with 4 of the 5 residues conserved among most of the 35 vertebrate telomerase RNAs. In this discussion, we considered CR7 as hTR nt 407–422; the CR7 element as originally defined (nt 400–429) contains the upper stem of the 3' pocket, which is a conserved element of the H/ACA motif. Of 13 known human H/ACA snoRNAs (Smith and Steitz, 1997), only U64 shares this remarkable degree of similarity with the hTR H/ACA domain 3' stem-loop. Indeed, we found that in the conserved CR7 loop, deletion of nt 411–418 ($\Delta$4) or substitution of nt 411–414 (UGAG to ACUC) prevented accumulation of any detectable hTR or telomerase activity in vivo. Thus, the CR7 element plays a telomerase-specific role in hTR processing or accumulation that is distinct from the role of the consensus H/ACA motif itself. As with the hTR H/ACA motif, however, the CR7 element was dispensable for telomerase activity in vitro.

Two separable regions of hTR interact independently with TERT in vivo and in vitro. Our in vivo hTR-TERT interaction studies revealed that two separable regions of hTR can each interact with TERT. This conclusion is confirmed by in vitro activity results, which demonstrated that hTR nt 1–209 and IH1 can stimulate as much activity in trans as in cis in the context of the full-length RNA. Because reconstitution of telomerase activity did not depend on the order of addition of nt 1–209 and IH1, we conclude that either fragment alone is capable of independent association with TERT.

The vertebrate-specific N-terminal region of TERT (amino acids 1–180) offers a binding site for the vertebrate-specific IH1 RNA element. This region is highly conserved among vertebrate TERTs sequenced to date. Because the IH1 element is required for telomerase activity both in vivo and in vitro, it provides target for telomerase inhibitor development. Telomerase inhibition has been demonstrated to halt the growth of several different cultured tumor cell types indicating its usefulness as an anti-cancer therapy. In addition, stimulating telomerase activity by affecting the IH1-TERT interaction can be used to treat proliferative deficiencies.

Here we demonstrate that the human telomerase RNA contains not one but two independent interaction sites for TERT. In vivo, the vertebrate-specific IH1 RNA element shows a somewhat more preferential association with TERT (in the context of the hTR H/ACA domain) than does hTR nt 1–209 (in the context of the hTR-U64 chimera). In vitro, these two hTR regions appear to bind TERT with similar affinities. Non-template residues of telomerase RNA have been demonstrated to be important for telomerase function in ciliate (Licht and Collins, 1999), yeast (Roy et al., 1998), and human telomerase RNAs (Mitchell et al., 1999a). However, our results are the first to reveal a functional requirement for an RNA sequence physically separable from the template. Furthermore, we demonstrate that the two RNA regions required for catalytic activity each interact with TERT and can do so in a largely noncooperative manner. Our data indicate that the hTR IH1 element can stimulate catalytic activity by directly or indirectly contributing to the binding or positioning of nucleotide and/or primer substrates, influencing template positioning, or enhancing processivity.

Experimental Procedures: Constructs. Expression constructs for hTR were derived from the Stu I-tagged, altered-template, Sac I-EcoRI hTR construct (nt 1–560) in the pRc/CMV expression vector described previously (Mitchell et al., 1999a). Mutagenesis was performed on double-stranded DNA with linear amplification from a pair of complementary oligonucleotides, followed by parental plasmid digestion with Dpn I. All constructs were resequenced to verify the intended nucleotide changes. The chimera constructs were derived from the hTR-U64 chimera also described previously (Mitchell et al., 1999a), which placed full-length U64 (nt 1 –134) in place of hTR nt 210–560 in the altered-template hTR construct described above. The hTR-U64-IH1 (sense IH1) and hTR-U64-αIH1 (antisense IH1) constructs were created by digesting the hTR IH1 element DNA template for T7 transcription (see below) with Nhe I and ligating it in both orientations into the hTR-U64 construct mutagenized (U64 nt 33–35 TCA to AGC) to create an Nhe I restriction site in the U64 5' hairpin terminal loop. Expression of the hTR H/ACA domain was directed by the Stu I-tagged Xba I-Eco RI restriction fragment (hTR nt 160–560) under transcriptional control of the human U6 promoter as described previously (Mitchell et al., 1999a). The FLAG-TERT expression construct was a gift from Amgen and includes a FLAG epitope tag at both N- and C-termini. Constructs for expression of HA-TERT in RRL were made by cloning the wild-type TERT coding region amplified from pBABE, a gift from the Weinberg lab, behind an N-terminal, HA epitope tag in pCITE4a (Novagen).

Transfection, immunopurification, RNA analysis and activity assays. Human 293 and VA13 cells were cultured in DMEM plus 10% fetal bovine serum and antibiotics. Calcium phosphate-mediated transient transfections, RNA preparation by acid guanidine thiocyanate-phenol chloroform extraction, preparation of cell extracts by freeze-thaw lysis, Northern blots, and telomerase activity assays were performed as described previously (Mitchell et al., 1999b). HA and FLAG immunopurifications from cell extracts were also performed as described previously (Mitchell et al., 1999b). Each transfection was performed multiple times.

In vitro reconstitution. Altered-template RNAs were transcribed in vitro using linearized plasmid DNA templates with T7 RNA polymerase (Stratagene). hTR nt 1–451, nt 1–209, nt 207–451 and IH1 RNAs were transcribed using the Ambion T7-MEGAshortscript kit according to the manufacturer's instructions. DNA templates for hTR nt 1–451 and nt 1–209 contained 5' extensions of the following vector-derived sequence: 5'-GGGAGACCCACT-3'. IH1 contained hTR nt 241–330 with the following Nhe I linker-derived 5' and 3' extensions, respectively: 5'-GGGCTAGC-3'; 5'-GCTAGCTAGT-3'. All RNAs were quantified using fluorometry, and relative concentrations were confirmed by dot-blot hybridization.

35S-methionine-labeled, N-terminally HA epitope-tagged TERT in pCITE4a was expressed using the TNT system (Promega) according to manufacturer's instructions for 1 hour at 30° C. A volume of 0.5 μL was aliquotted into tubes containing in vitro transcribed RNA(s) and 1× Buffer E (50 mM NaCl, 20 mM Hepes pH 8.0, 2 mM MgCl2, 0.2 mM EGTA, 2 mM DTT and 10% glycerol) in a final volume of 2.5–3.0 μUL. RNP assembly reactions were incubated for 30 min at 30° C. and aliquots measured for telomerase activity by TRAP.

In the order-of-addition experiment, HA-TERT was expressed in the TNT system as above. A volume of 2 μL was assembled on ice with 1μM final assembly reaction concentration of each in vitro transcribed RNA(s) and 1× final concentration Buffer E in 4 μL. Following the RNP assembly reaction for 30 min at 30° C., TERT-RNA complexes were bound to a minimal volume of HA antibody-bound GammaBind G Sepharose (Pharmacia) at room temperature for 1 hour then washed 3 times with 1× Buffer E. Washed samples were either left on ice or subjected to a second assembly reaction. These subsequent RNP assembly reactions each contained 1 μL fresh rabbit reticulocyte lysate and either 1 μM final assembly reaction concentration of transactivating RNA, or a mixture of equal bead volumes of assembled HA-TERT/RNA complexes without the further addition of RNA. Following the second 30 min incubation at 30° C., these TERT-RNA complexes were washed again. Bead-bound complexes were withdrawn each at dilutions of 1/100, 1/20 and 1/5 and assayed by TRAP. The order-of-addition experiment was repeated in the absence of RRL using HA-TERT immunopurified on HA antibody resin and washed as described above, without the addition of RRL to either the first or second RNP assembly reaction.

1. Protocol for high-throughput human telomere polymerization assay.

A. Reagents:

Neutralite Avidin: 20 μg/ml in PBS.

human telomerase: $10^{-8}$–$10^{-5}$ M human telomerase comprising truncated RNA component in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1 mM dATP, 1 mM dTTP, 1% glycerol, 0.5% NP-40, 50 mM BME, 1 mg/ml BSA, cocktail of protease inhibitors.

[$^{32}$P]α-dGTP 10×stock: 2×10$^{-5}$ M "cold" dGTP with 100 μCi [$^{32}$P]α-dGTP. Place in the 4° C. microfridge during screening.

telomerase substrate: 10$^{-7}$–10-4 M biotinylated telomerase substrate (5'-biotin-d(TTAGGG)$_3$-3'] in PBS.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of assay plates:

Coat with 120 μl of stock N Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl human telomerase (1–1000 fmoles/40 ul in assay buffer)

Add 10 μl compound or extract.

Add 10 μl[$^{32}$P]α-dGTP 10×stock.

Add 40 μl biotinylated telomerase substrate (0.1–10 p moles/40 ul in assay buffer)

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for all assays (located on each plate):

a. Non-specific binding b. cold dGTP at 80% inhibition.

2. Protocol for high throughput human telomerase subunit-RNA complex formation assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.

$^{33}$P human telomerase polypeptide 10×stock: 10$^{-8}$–10$^{-6}$ M "cold" human telomerase polypeptide (TERT or dyskerin) supplemented with 200,000–250,000 cpm of labeled polypeptide (Beckman counter). Place in the 4° C. microfridge during screening.

Protease inhibitor cocktail (1000×: 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

telomerase RNA: 10$^{-7}$–10$^{-4}$ M biotinylated truncated telomerase RNA in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-human telomerase polypeptide (20,000–25,000 cpm/0.1–10 pmoles/well=10$^{-9}$–10$^{-7}$ M final concentration).

Shake at 25° C. for 15 minutes.

Incubate additional 45 minutes at 25° C.

Add 40 μl biotinylated RNA (0.1–10 pmoles/40 ul in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate):

a. Non-specific binding b. Soluble (non-biotinylated RNA) at 80% inhibition.

REFERENCES

Artandi, S. E., and DePinho, R. A. (2000) Curr. Opin. Genet. Dev. 10, 39–46.

Balakin, A., Smith, L., and Fournier, M. (1996) Cell 86, 823–834.

Beattie, T. L., Zhou, W., Robinson, M. O., and Harrington, L. (1998) Curr. Biol. 8, 177–180.

Bortolin, M. L., Ganot, P., and Kiss, T. (1999) EMBO J. 18, 457–69.

Bryan, T. M., and Cech, T. R. (1999) Curr. Opin. Cell Biol. 11, 318–324.

Bryan, T. M., et al. (1995) EMBO J. 14, 4240–4248.

Chen, J. -L., Blasco, M. A., and Greider, C. W. (2000) Cell 100, 503–514.

Colgin, L. M., and Reddel, R. R. (1999) Curr. Opin. Genet. Dev. 9, 97–103.

Collins, K. (2000) Curr. Opin. Cell Biol. 12, 378–383.

Dokal, I. (1999) British Journal of Haematology 105, 11–15.

Feng, J., et al. (1995) Science 269, 1236–1241.

Ganot, P., Bortolin, M.-L., and Kiss, T. (1997a) Cell 89, 799–809.

Ganot, P., Caizergues-Ferrer, M., and Kiss, T. (1997b) Genes Dev. 11, 941–956.

Greider, C. W. (1995) In Telomeres, E. H. Blackburn and C. W. Greider, eds. (Cold Spring Harbor, N.Y.: Cold Spring Harbor Laboratory Press), pp. 35–68.

Greider, C. W., and Blackburn, E. H. (1989) Nature 337, 331–337.

Hinkley, C., et al. (1998) Nuc. Acids Res. 26, 532–536.

Holt, S. E., et al. (1999) Genes Dev. 13, 817–826.

Kim, N. W., et al. (1994) Science 266, 2011–2014.

Lafontaine, D. L. J., et al. (1998) Dev. 12, 527–537.

Licht, J. D., and Collins, K. (1999) Genes Dev. 13, 1116–1125.

Lingner, J., Hendrick, L. L., and Cech, T. R. (1994) Genes Dev. 8, 1984–1998.

Lingner, J., et al.(1997) Science 276, 561–567.

Mitchell, J. R., Cheng, J., and Collins, K. (1999a) Mol. Cell. Biol. 19, 567–576.

Mitchell, J. R., Wood, E., and Collins, K. (1999b) Nature 402, 551–555.

Romero, D. P., and Blackburn, E. H. (1991) Cell 67, 343–353.

Roy, J., Fulton, T. B., and Blackburn, E. H. (1998) Genes Dev. 12, 3286–3300.

Smith, C. M., and Steitz, J. A. (1997) Cell 89, 669–672.

Tesmer, V. M., et al. (1999) Mol. Cell. Biol. 19, 6207–6216.

Tollervey, D., and Kiss, T. (1997) Curr. Opin. Cell Biol. 9, 337–342.

Weinrich, S. L., et al. (1997) Nat. Genet. 17, 498–502.

Zaug, A., Lingner, J., and Cech, T. (1996) Nuc. Acids Res. 24, 532–533.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

5. A method according to claim 3, wherein the compound-biased binding affinity is detected inferentially as telomerase catalytic activity.

6. A method according to claim 3, wherein the compound-biased binding affinity is detected inferentially as telomerase catalytic activity and the mixture is in vitro.

7. A method according to claim 3, wherein the compound-biased binding affinity is detected inferentially as telomerase catalytic activity and the mixture is within a viable cell.

8. A human telornerase RNA fragment consisting of a telomerase reverse transcriptase protein binding domain consisting of nucleotides 241–330 of SEQ ID NO:1.

9. A mixture of a human telomerase reverse transcriptase protein and a RNA fragment according to claim 8, wherein the protein and RNA fragment specifically interact.

10. A method for identifying modulators of a human telomerase reverse transcriptase protein-human telomerase RNA interaction, the method comprising the steps of:

What is claimed is:

1. A human telomerase RNA fragment consisting of a telomerase reverse transcriptase protein binding domain consisting essentially of nucleotides 241–330 of SEQ ID NO:1.

2. A mixture of a human telomerase reverse transcriptase protein and a RNA fragment according to claim 1, wherein the protein and RNA fragment specifically interact.

3. A method for identifying modulators of a human telomerase reverse transcriptase protein-human telomerase RNA interaction, the method comprising the steps of:

incubating a mixture according to claim 2 with compound under conditions whereby, but for the presence of said agent, said protein specifically binds said RNA fragment at a control binding affinity; and detecting the binding affinity of the protein to the RNA fragment to determine a compound-biased binding affinity, wherein a difference between the compound-biased binding affinity and the control binding affinity indicates that the compound modulates the binding of the protein to the RNA fragment.

4. A method according to claim 3, wherein the compound-biased binding affinity is detected directly by solid phase binding assay.

incubating a mixture according to claim 9 with a compound under conditions whereby, but for the presence of said compound, said protein specifically binds said RNA fragment at a control binding affinity; and detecting the binding affinity of the protein to the RNA fragment to determine a compound-biased binding affinity, wherein a difference between the compound-biased binding affinity and the control binding affinity indicates that the compound modulates the binding of the protein to the RNA fragment.

11. A method according to claim 10, wherein the compound-biased binding affinity is detected directly by solid phase binding assay.

12. A method according to claim 10, wherein the compound-biased binding affinity is detected inferentially as telornerase catalytic activity.

13. A method according to claim 10, wherein the compound-biased binding affinity is detected inferentially as telomerase catalytic activity and the mixture is in vitro.

14. A method according to claim 10, wherein the compound-biased binding affinity is detected inferentially as telomerase catalytic activity and the mixture is within a viable cell.

* * * * *

UNITED STATES PATENT AND TRADEMARK OFFICE
CERTIFICATE OF CORRECTION

PATENT NO.     : 6,342,358 B1                                        Page 1 of 1
DATED          : January 29, 2002
INVENTOR(S)    : Kathleen Collins et al.

It is certified that error appears in the above-identified patent and that said Letters Patent is hereby corrected as shown below:

<u>Column 17,</u>
Lines 52-64, the correct claim 3 is as follows:

3. A method for identifying modulators of a human telomerase reverse transcriptase protein-human telomerase RNA interaction, the method comprising the steps of:
   incubating a mixture according to claim 2 with a compound under conditions whereby, but for the presence of said compound, said protein specifically binds said RNA fragments at a control binding affinity; and
   detecting the binding affinity of the protein to the RNA fragment to determine a compound-biased binding affinity, wherein a difference between the compound-biased binding affinity and the control binding affinity indicates that the compound modulates the binding of the protein to the RNA fragment <u>Column 18,</u>
Lines 8-11, the correct claim 8 is as follows:

8. A human telomerase RNA fragment consisting of a telomerase reverse transcriptase protein binding domain consisting of nucleotides 241-330 of SEQ ID NO:1.

Lines 57-59, the correct claim 12 is as follows:

12. A method according to claim 10, wherein the compound-biased binding affinity is detected inferentially as telomerase catalytic activity.

Signed and Sealed this

Twenty-fourth Day of December, 2002

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 451
<212> TYPE: RNA
<213> ORGANISM: human

<400> SEQUENCE: 1

```
ggguugcgga ggguggcccu gggaggggug guggccauuu uuugucuaac ccuaacugag      60
aagggcguag gcgccgugcu uuugcuccc  gcgcgcuguu uuucucgcug acuuucagcg     120
ggcggaaaag ccucggccug ccgccuucca ccguucauuc uagagcaaac aaaaaauguc    180
agcugcuggc ccguucgccc cucccgggga ccugcggcgg gucgccugcc cagccccga     240 accccgccug gaggccgcgg ucggcccggg gcuucuccgg aggcacccac ugccaccgcg    300
aagaguuggg cucugucagc cgcgggucuc ucgggggcga gggcgagguu caggccuuuc    360
aggccgcagg aagaggaacg gagcgagucc ccgcgcgcgg cgcgauuccc ugagcugugg    420
gacgugcacc caggacucgg cucacacaug c                                   451
```